United States Patent [19]

Cruthers et al.

[11] 4,173,632

[45] Nov. 6, 1979

[54] FASCIOLICIDAL COMPOSITIONS

[75] Inventors: Larry R. Cruthers; Terrence M. James, both of Flemington, N.J.; Sidney Goff, New Hope, Pa.; Antoine R. Alouche, Sao Paulo, Brazil

[73] Assignee: E. R. Squibb & Sons, Inc., Princeton, N.J.

[21] Appl. No.: 929,876

[22] Filed: Jul. 31, 1978

[51] Int. Cl.² .................... A61K 31/62; A61K 31/415
[52] U.S. Cl. .................... 424/232; 424/230; 424/273 B
[58] Field of Search ............ 424/273 B, 232, 230

[56] References Cited

PUBLICATIONS

Gyurik et al.–Chem. Abst., vol. 85, (1976), p. 88534r.

*Primary Examiner*—Sam Rosen
*Attorney, Agent, or Firm*—Lawrence S. Levinson; Burton Rodney

[57] ABSTRACT

Anthelmintic compositions which are especially useful for their fasciolicidal activity are provided and are formed of a synergistic combination of 5(6)-lower alkylbenzimidazol carbamates, such as (5-butyl-1H-benzimidazol-2-yl)carbamic acid, methyl ester, and 3,5-dibromo-N-(4-bromophenyl)-2-hydroxybenzamide(tribromosalan) alone or in admixture with 4',5-dibromosalicylanilide and/or 3,5-dibromosalicylanilide.

8 Claims, No Drawings

FASCIOLICIDAL COMPOSITIONS

BACKGROUND OF THE INVENTION

U.S. Pat. Nos. 3,480,642, 3,574,845 and 3,682,952 disclose various benzimidazole carbamates, including lower alkyl benzimidazole carbamates, for example, (5-butyl-1H-benzimidazol-2-yl)carbamic acid, methyl ester as possessing anthelmintic properties and useful in the treatment of *Syphacia obvelata* and *Aspicularis tetraptera* (mouse pinworm), *Nematospiroides dubius*, the migratory stages of *Ascaris suum, Toxocara canis, Ancylostoma caninum, Trichuris vulgaris*, Physaloptera spp, *Haemonchus contortus*, Ostertagia spp, Trichostrongylus spp, Nematodirus spp, *Trichuris ovis*, Cooperia spp, *Strongyloides papillosus, Bunostomum trigonocephalum* and Oesophagostomum spp.

Unfortunately, the compounds described above have been found to have only marginal activity against sheep liver fluke (*Fasciola hepatica*) and other liver flukes and thus are not recommended for use against such infestations.

Tribromosalan (3,5-dibromo-N-(4-bromophenyl)-2-hydroxybenzamide or 3,4',5-tribromosalicylanilide) originally disclosed in U.S. Pat. Nos. 2,967,885, 3,064,048 and 3,057,920 has been found to be somewhat active in treating Fasciola infections as disclosed in the following papers: J. Hildebrandt, The Veterinary Record, June 15, 1968, pp. 699–700; J. C. Boray et al, The Veterinary Record, Feb. 6, 1965, pp. 175–177; and J. C. Boray et al, The Veterinary Record, Feb. 11, 1967, pp. 218–224.

DESCRIPTION OF THE INVENTION

Surprisingly, it has now been found that whereas 5(6)-lower alkyl-benzimidazol carbamates, such as (5-n-butyl-1H-benzimidazol-2-yl)carbamic acid methyl ester, alone are practically speaking ineffective as fasciolicides, and tribromosalan alone or together with 4',5-dibromosalicylanilide and/or 3,5-dibromosalicylanilide is only marginally effective as a fasciolicide, a combination of one or more 5(6)-lower alkyl benzimidazol carbamates and tribromosalan alone or together with 4',5-dibromosalicylanilide and/or 3,5-dibromosalicylanilide, (tribromosalan alone or in such mixtures being hereinafter referred to as the bromosalan component), is 100% efficacious against adult liver flukes. Accordingly, such combination is synergistic in that each component of the combination substantially and materially enhances the fasciolicidal activity of the other, so that the combination of the invention has surprisingly substantially greater fasciolicidal activity than each of the components of the combination taken alone as well as the additive activities of each of such components.

The benzimidazoles which may be employed in the synergistic combination of the invention are disclosed in U.S. Pat. Nos. 3,480,642, 3,574,845 and 3,682,952 and will have the following structure:

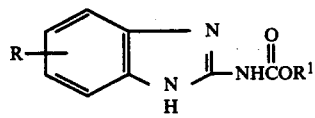

wherein R is in the 5- or 6-position and is lower alkyl and R¹ is lower alkyl or phenyl lower alkyl.

The term "lower alkyl" or "alkyl" as used herein whether employed as an independent substituent or as a part of another substituent includes straight or branched chain aliphatic hydrocarbon radicals having up to and including 7 carbon atoms, preferably 1 to 3 carbons, such as methyl, ethyl, propyl, isopropyl, butyl, isobutyl, t-butyl, amyl, hexyl, heptyl and the like.

The term "phenyl lower alkyl" refers to a phenyl group linked to a "lower alkyl" group as defined above.

The tribromosalan (3,5-dibromo-N-(4-bromophenyl)-2-hydroxybenzamide) the other component of the combination has the formula

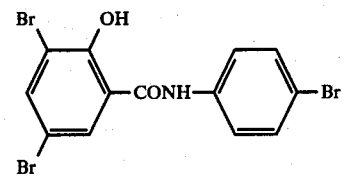

The tribromosalan may be used as such or in combination with 4',5-dibromosalicylanilide and/or 3,5-dibromosalicylanilide. The tribromosalan will be employed in such bromosalan mixtures in amounts ranging from about 70 to about 90% preferably from about 78 to about 82% by weight of the bromosalan mixture, while the 4,5-dibromosalicylanilide may be employed in amounts ranging from about 10 to about 25%, and preferably from about 13 to about 19% by weight of the bromosalan mixture, and the 3,5-dibromosalicylanilide may be employed in amounts ranging from about 2 to about 10%, and preferably from about 3 to about 5% by weight of the bromosalan mixture.

In the synergistic combination of the invention, the 5(6)-lower alkyl benzimidazol carbamate will be employed in amounts ranging from about 5 to about 30% and preferably from about 8 to about 15% by weight of the combination, and the total bromosalan content will be employed in amounts ranging from about 10 to about 50% and preferably from about 12 to about 24% by weight of the combination. Thus, the bromosalan component is employed in a weight ratio to the lower alkyl benzimidazol carbamate of within the range of from about 2:1 to about 10:1, and preferably from about 2:1 to about 5:1.

The synergistic combination of the invention has anthelmintic activity and is useful in the treatment and/or prevention of helminthiasis, a parasitic disease which causes widespread and often serious infection in domesticated animals such as swine, horses, cattle, dogs, cats and sheep. The combination is useful in treating infections caused by Haemonchus, Ostertagia, Trichostrongylus, Cooperia, Dictyocaulus, Nematodirus, Bunostomum, Strongyloides, Oesophagostomum, Trichuris, Moniezia, and liver flukes (for example in sheep). As indicated hereinbefore, in the treatment of liver flukes, the combination of the invention has been found to be synergistic in that it possesses fasciolicidal activity which is far superior than would be expected from the additive effect of the separate components of the combination.

In treating domesticated animals, the combination is given orally; however, other routes such as parenterally, for example, subcutaneously, intravenously, interperitoneally and intramuscularly may be employed.

Where the combination is administered orally, it may be mixed with a nontoxic, edible carrier to form a feed supplement, or may be administered in unit dosage forms such as powders, capsule, tablet, boluses, drenches, etc.

Where the combination is administered parenterally, it may be dispersed (for example, suspended) in non-toxic non-pyrogenic physiologically acceptable carriers such as water, benzyl benzoate, 1,3-butylene glycol, ethyl oleate, glyceryl triacetate, castor oil, sesame oil, and sesame oil:benzyl benzoate (1:1). The parenteral product will usually take the form of a suspension containing from about 1 to about 10% by weight of the combination in anyone or mixture of the above carriers.

In general, the combination of the invention exhibits anthelmintic activity when administered to animals (parenterally or orally) in a single dose of about 1 to about 100 mg per kilogram of animal body weight. It is preferred to employ in the range of 20–75 mg per kilogram of body weight to achieve the synergistic effect with respect to fasciolicidal activity. The combination may be divided into a plurality of smaller doses given parenterally or orally over one or more days.

When the combination is to be administered in unit dosage form, capsules, boluses or drenches containing the desired amount of anthelmintic distributed in a pharmaceutically acceptable vehicle are usually employed. These are prepared by intimately and uniformly mixing the active ingredient with suitable finely divided diluents, suspending agents, fillers, disintegrating agents and/or binders such as starch, lactose, talc, magnesium stearate, vegetable gums and the like and are compounded by techniques generally known in the art.

The combination of the invention may also be administered as a component of the feed of the animals or suspended in the drinking water. Thus, novel feed and feed supplement compositions may be prepared in which the combination of the invention is present as an active anthelmintic ingredient. A typical feed supplement comprises the anthelmintic agent intimately dispersed in or admixed with an inert carrier or diluent, i.e., one that is nonreactive with respect to the anthelmintic agent and that may be administered with safety to the animals. The carrier or diluent is preferably one that is or may be an ingredient of an animal ration. This composition may be mixed with the feed to give any useful desired concentration, preferably about 0.1–2%. Lastly, feeds containing the active ingredients may be made directly by mixing said active ingredients in a feed which is inert to said anthelmintic compounds so as to give feeds having concentrations of anthelmintic agent of from 0.1–2%.

The following Example is provided for illustrative purposes and may include particular features of the invention, however, the example should not be construed as limiting the inventions, many variations of which are possible without departing from the spirit or scope thereof. All temperatures are in degrees centigrade.

EXAMPLE

The following Example is carried out to show the synergistic fasciolicidal activity of the combination of the invention in adult sheep infected with Fasciola hepatica.

Each of the adult sheep tested is inoculated with 250 viable metacercariae at least 20 weeks prior to drug evaluation. All sheep are confirmed positive by fecal egg sedimentations prior to the initiation of the test.

Several formulations are prepared and administered to infected sheep as follows:

(1) A 9% aqueous suspension of (5-butyl-1H-benzimidazol-2-yl)carbamic acid, methyl ester, hereinafter referred to as Control A, is evaluated in one sheep.

(2) A 12% aqueous suspension of bromosalan component containing about 80% 3,4',5-tribromosalicylanilide, about 16% 4,5-dibromosalicylanilide, and about 4% 3,5-dibromosalicylanilide, hereinafter referred to as Control B, is evaluated in two sheep at 30 mg/kg.

(3) An aqueous suspension containing 9% (5-butyl-1H-benzimidazol-2-yl)carbamic acid, methyl ester and 12% bromosalan component containing about 80% 3,4',5-tribromosalicylanilide, about 16% 4,5-dibromosalicylanilide, and about 4% 3,5-dibromosalicylanilide, hereinafter referred to as "EXAMPLE," is evaluated in two sheep at 30 mg/kg and in two sheep at 60 mg/kg.

(4) In addition, as a further control, rafoxanide (N-[3-chloro-4-(4-chlorophenoxy)phenyl]-2-hydroxy-3,5-diiodobenzamide) in a 2.27% W/V mixture, referred to as Flukanide (Control C) is used in one sheep as the positive control drug.

Infected, unmedicated sheep are maintained for efficacy calculations.

All sheep are sacrificed 7 days post-treatment. The liver of each animal is removed and the bile ducts split open with a scissors. All flukes are picked out of the bile ducts and preserved in 10% formalin. The liver, after inspection of the bile ducts, is cut into small pieces which are squeezed by hand and placed in a bucket of warm water for 20 minutes. These tissue pieces are then placed in a 60-mesh sieve and sprayed with warm water and all whole or cut flukes are recovered. Only intact flukes or portions with oral suckers are counted as flukes. All gall bladder contents are examined microscopically for flukes or fluke eggs. Anthelmintic efficacy is calculated by comparison of the worm burden of the infected, unmedicated control sheep with those of the treated groups.

Test results indicate that rafoxanide (Control C) and the Example suspensions (containing (5-butyl-1H-benzimidazol-2-yl)carbamic acid, methyl ester and bromosalan component) (at both 30 and 60 mg/kg) are 100% efficacious against adult liver flukes. The Control A formulation containing only (5-butyl-1H-benzimidazol-2-yl)carbamic acid, methyl ester is found to be only 65% efficacious against adult liver flukes, at 15 mg/kg, while the Control B formulation containing only the bromosalan component is found to be only 87% and 0% (average 43.5%) effective at 30 mg/kg against adult liver flukes.

The above results show that while (5-butyl-1H-benzimidazol-2-yl)carbamic acid, methyl ester by itself and the bromosalan component by itself are only marginally (and not commercially) effective as fasciolicides, the combination of these two components, surprisingly, and unexpectedly is 100% efficacious against adult liver flukes and therefore commercially useful as a fasciolicide. The above clearly shows the unpredictable synergistic activity of the combination of the invention.

In a manner similar to the foregoing, combinations of other lower alkyl benzimidazol carbamates with the bromosalan component produce synergistic fasciolicidal results. Examples of other lower alkyl benzimidazol carbamates which may be included in synergistic combination with tribromosalan include (5-ethyl-1H-benzimidazol-2-yl)carbamic acid, methyl ester;
(5-methyl-1H-benzimidazol-2-yl)carbamic acid, methyl ester;
(5-propyl-1H-benzimidazol-2-yl)carbamic acid, ethyl ester;
(5-pentyl-1H-benzimidazol-2-yl)carbamic acid, methyl ester;
(5-butyl-1H-benzimidazol-2-yl)carbamic acid, benzyl ester.

What is claimed is:

1. A fasciolicidal combination comprising a 5(6)-lower alkyl benzimidazol carbamate having the formula

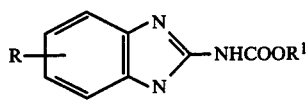

wherein R is in the 5- or 6-position and is lower alkyl, and $R^1$ is lower alkyl or phenyl lower alkyl, in combination with a bromosalan component commprising 3,5-dibromo-N-(4-bromophenyl)-2-hydroxybenzamide alone or in admixture with 4',5-dibromosalicylanilide, and/or 3,5-dibromosalicylanilide, wherein the bromosalan component is present in a weight ratio to the 5(6)-lower alkyl benzimidazol carbamate of within the range of from about 2:1 to about 10:1.

2. The combination as defined in claim 1 wherein the benzimidazol carbamate is (5-butyl-1H-benzimidazol-2-yl)carbamic acid, methyl ester.

3. The combination as defined in claim 1 wherein the 5(6)-lower alkyl benzimidazol carbamate is present in an amount within the range of from about 5 to about 30% by weight of the combination and the bromosalan component is present in an amount within the range of from about 10 to about 50% by weight of the combination.

4. The combination as defined in claim 1 wherein the bromosalan component comprises from about 70 to about 90% 3,5-dibromo-N-(4-bromophenyl)-2-hydroxybenzamide, from about 10 to about 25% by weight, 4',5-dibromosalicylanilide, and from about 2 to about 10% by weight 3,5-dibromosalicylanilide.

5. The combination as defined in claim 1 wherein the bromosalan component comprises from about 78 to about 82% 3,5-dibromo-N-(4-bromophenyl)-2-hydroxybenzamide, from about 13 to about 19% by weight 4',5-dibromosalicylanilide, and from about 3 to about 5% by weight 3,5-dibromosalicylanilide.

6. A fasciolicidal composition comprising a therapeutic amount of the fasciolicidal combination as defined in claim 1 and a pharmaceutically acceptable carrier therefor.

7. A method for treating or preventing fasciola infestation in mammalian hosts which comprises administering to a mammal a therapeutic amount of a fasciolicidal composition as defined in claim 6.

8. The method as defined in claim 7 wherein said composition is administered orally or parenterally.

* * * * *